еe
United States Patent [19]
Subramanian et al.

[11] 3,974,268

[45] Aug. 10, 1976

[54] BONE-SEEKING TECHNETIUM-99M IMIDODIPHOSPHONATE COMPLEX

[75] Inventors: Gopal Subramanian, Manlius; John Gilmore McAfee, Fayetteville, both of N.Y.

[73] Assignee: Research Corporation, New York, N.Y.

[22] Filed: May 30, 1975

[21] Appl. No.: 582,176

[52] U.S. Cl. ............................. 424/1; 250/303; 252/301.1 R; 423/302
[51] Int. Cl.[2] ................... A61K 43/00; G01T 1/16; C01B 21/10
[58] Field of Search .................. 424/1; 252/301.1 R; 260/429 R; 250/303; 423/302

[56] References Cited
UNITED STATES PATENTS

| | | | |
|---|---|---|---|
| 3,125,412 | 3/1964 | Nielsen | 423/302 |
| 3,735,001 | 5/1973 | McRae et al. | 424/1 |

FOREIGN PATENTS OR APPLICATIONS

| | | | |
|---|---|---|---|
| 840,386 | 7/1960 | United Kingdom | 423/302 |

OTHER PUBLICATIONS

Hegesippe et al., Journal of Nuclear Biology and Medicine, vol. 17, No. 3, 1973, pp. 93–96.
Subramanian et al., Radiology, vol. 99, No. 1, Apr. 1971, pp. 192–196.
Castronovo et al., Journal of Nuclear Medicine, vol. 13, No. 11, 1972, pp. 823–827.
Subramanian et al., Radiology, vol. 102, Mar. 1972, pp. 701–704.
King et al., Journal of Nuclear Medicine, vol. 14, No. 9, 1973, pp. 695–698.
Stevenson et al., Journal of Nuclear Medicine, vol. 14, No. 10, 1973, pp. 774–775.
Zimmer et al., Chemical Abstracts, vol. 83, No. 20, Nov. 17, 1975, p. 282, abstract No. 168552u.

*Primary Examiner*—Benjamin R. Padgett
*Assistant Examiner*—Christine M. Nucker
*Attorney, Agent, or Firm*—Dennis P. Clarke

[57] ABSTRACT

Technetium-99m-imido disphosphonate complex useful as a skeletal-imaging agent, particularly useful for diagnostic purposes.

11 Claims, 3 Drawing Figures

3,974,268

BONE-SEEKING TECHNETIUM-99M IMIDODIPHOSPHONATE COMPLEX

BACKGROUND OF THE INVENTION

Recently, various organic phosphate and phosphonate complexes of technetium-99m have been suggested as gamma-emitting radionuclide agents for skeletal imaging. The excellent physical characteristics (half-life of 6 hours and monoenergetic gamma emission of 140 KeV with an external photon yield of 90%) of the readily available radionuclide technetium-99m render it an attractive substitute for the conventionally employed long-lived nuclide strontium 85 (half-life 65 days) and the inconveniently short-lived fluorine 18 (half-life 1.83 hours). By virtue of its optimum half-life characteristics and absence of beta emission, technetium-99m can be administered in relatively large doses (10–15 mCi) without exceeding reasonable radiation levels.

Until fairly recently, technetium-99m has been used almost exclusively in radioisotopic imaging procedures for almost every major organ in man with the exception of the skeleton. Recently, however, various organic phosphate and phosphonate complexes of technetium-99m have been employed for skeletal imaging purposes. (Perez et al., *J. Nucl. Med.* 13:788–789, 1972; Subramanian et al., Radiology, 98:192–196, 1971; Subramanian et al., *Radiology*, 102:701–704, 1972; Subramanian et al., *J. Nucl. Med.*, 13:947–950, 1972; Tofe et al., *J. Nucl. Med.*, 15:69–74, 1974; Yano, *J. Nucl. Med.* 14:73–78, 1973; Castronova et al., *J. Nucl. Med.* 13:823–827, 1972; and Subramanian et al., *J. Nucl. Med.*, August, 1975 (U.S. application Ser. No. 368,473, filed June 11, 1973).

It was found that when solutions of these technetium-99m phosphate and phosphonate complexes are given intravenously, the technetium-99m localizes to a great extent in bone, particularly in diseased or abnormal areas of the skeleton. Good visualization of both normal bone and skeleton lesions is observed about 2 hours after administration of the complexes. Normal and abnormal skeletal tissues are readily delineated using conventional radioisotope imaging devices such as rectilinear scanners or scintillation cameras.

There has been a continuing search in this area for technetium-99m complexes having a higher bone uptake than those currently employed in the art.

SUMMARY OF THE INVENTION

It has been found that a technetium-99m-tin-imidodiphosphonate complex is a highly effective skeletal imaging agent having a high uptake in bone.

The invention also relates to stannous imidodiphosphonate complex employed as an intermediate for preparing the technetium-99m-tin-imidodiphosphonate complex.

The invention includes a method for preparing the technetium-99m-tin-imidodiphosphonate complex by reducing a technetium-99m containing pertechnetate salt with stannous ion in an aqueous medium in the presence of imidodiphosphonic acid or a salt thereof.

The invention also relates to a bone-seeking composition comprising a solution adapted for intravenous administration containing the technetium-99m-tin-imidodiphosphonate complex.

Moreover, the invention relates to a method of skeletal imaging which includes the intravenous administration of a solution adapted for intravenous administration containing the technetium-99m-tin-imidodiphosphonate complex.

DETAILED DESCRIPTION OF THE INVENTION

Figure 1:
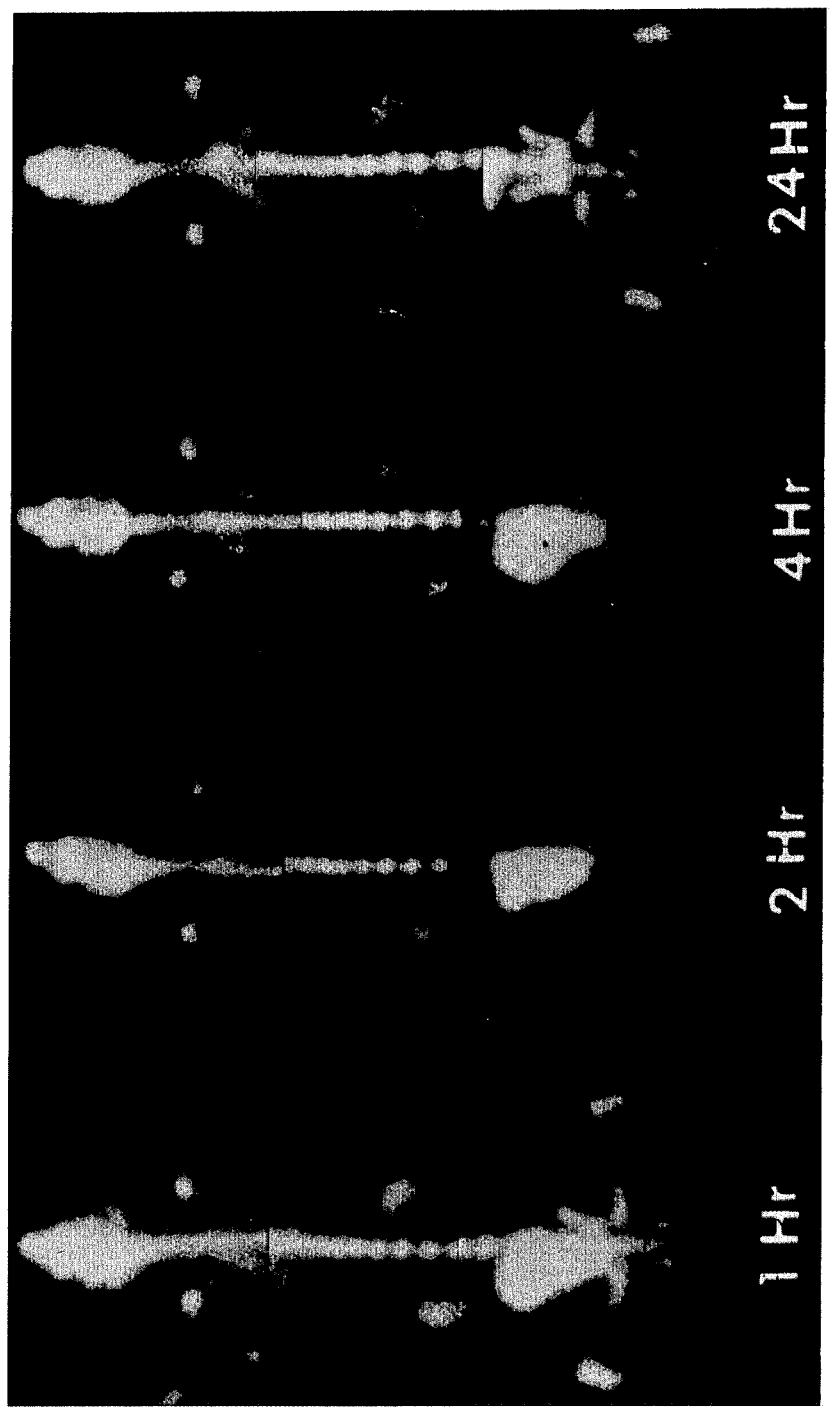

The complexing agent for forming the composition of the invention is imidodiphosphonic acid having the following structural formula:

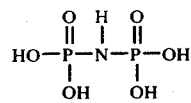

This complexing agent is also referred to in the art as "imidodiphosphate" (Reynolds et al., Calc. Tissue Research, 10:302–313 (1972); Larsen et al., Science, 166:1610, Dec. 19, 1969; Robertson et al., Biochem. Biophys. Acta, 222:677–680, 1970.). For example, the tetrasodium salt of the free acid is marketed by Boehringer-Mannheim Corporation, New York, as an "imidodiphosphate". The free acid and its salts are freely available or it may be prepared according to the method of Neilsen et al., JACS, 83:99–102, 1961. It is to be understood that the imidodiphosphonate complexes of the invention may be formed from the free imidodiphosphonic acid or suitable non-toxic, pharmaceutically acceptable salts thereof such as sodium, etc.

Technetium-99m is commercially available either from an isotope generator as a daughter product of molybdenum-99 or as a direct product from a commercial supplier. It is also available as a solvent extraction product from molybdenum-99 solutions generally as alkaline metal pertechnetate solutions at 5–100 mCi. A further discussion of preparative methods appears in U.S. Pat. Nos. 3,468,808 and 3,382,152.

Commercially available stannous salts, both hydrate and anhydrous, may be used as the tin source. Most readily available are stannous chloride, sulfate and acetate.

The composition of the invention is most conveniently provided in sterile kit form consisting of non-radioactive chemicals for mixing with a pertechnetate prior to use. The kit may contain stannous salt solution, imidodiphosphonate solution, alkaline and/or buffer solution, or combinations thereof. Using sterile pyrogen free water and reagents and using ascetic techniques, these solutions can be mixed with each other and then with the pertechnetate solution immediately prior to imaging. The particular order of mixing is not critical. Thus, the stannous salt could be added to the pertechnetate solution and the mixture combined with the imidodiphosphonate solution. Alternatively, the imidodiphosphonate could be combined with the pertechnetate prior to the addition of the stannous salt or combined with the stannous salt and admixed with the pertechnetate. One particularly preferred embodiment is a freeze-dried kit of stannous-imidodiphosphonate complex formed from the tetrasodium salt of the imidodiphosphonic acid and stannous chloride. The solution of the stannous imidodiphosphonate complex is freeze-dried and may be admixed with the pertechnetate solution immediately prior to skeletal imaging by the X-ray technician. The kits are prepared under sterile conditions and the final pH of the preparation is adjusted to 6.5 before freeze-drying. To form the complex, one simply adds to the kit vial the desired activity of technetium-99m in 2–5 ml volume and mixes well. The labeling yield is better than 98% and very little free pertechnetate is detectable.

The following is a non-limiting example of a method of preparation of the composition of the invention.

EXAMPLE 1

125 mg of tetrasodium imidodiphosphonate and 2.5 mg of Sn $Cl_2.2H_2O$ (HCl acid solution) were dissolved in 30 ml of water. The pH was adjusted to 6.5 and the volume brought up to 50 ml. 2 ml aliquots of the stannous imidodiphosphonate complex solution (containing 5 mg tetrasodium imidodiphosphonate and 100 $\mu g$ Sn $Cl_2.2H_2O$) were pipetted into 20 vials and lyophilized overnight. The imaging agents employed in the following examples were prepared by adding to each vial the desired activity of technetium-99m in 2–5 ml volumes and mixing well. The solutions were sterilized by passage through a 0.22 size membrane filter. After labeling, the pH of the solutions ranged from 6.2 to 6.5.

The above prepared complexes were utilized in the examples set forth below.

The organ distribution of the $^{99m}Tc$ imidodiphosphonate (IDP) was studied after I.V. injection of 50–200 $\mu Ci$ containing 0.1–0.2 mg of IDP per animal in New Zealand adult albino rabbits weighing 3.5–5 kg and compared with 10–20 $\mu Ci$ of $^{85}Sr$ administered simultaneously as a biological standard. The methods of tissue assay used were those described in the Subramanian et al. references, supra. These animals were sacrificed at various time intervals from 15 min. to 24 hrs. after injection. Because of the excellent skeletal uptake of $^{99m}Tc$ IDP in rabbits, a dog weighing 25 kgs was also imaged to evaluate the biological behavior of this compound in a higher mammal than the rabbit. A whole body image of the dog was obtained in the right lateral projection 4 hours after intravenous injection of 5 mCi of $^{99m}Tc$-IDP using the Ohio Nuclear Model 100 area scan camera fitted with a 140 kev high sensitivity parallel hole collimator, with the data density setting of 200.

A toxicological study was conducted in both mice and rabbits by serial injection of graduated doses and the acute toxicity of imidodiphosphonate (LD 50/30) was determined to be 45–50 mg imidodiphosphonic acid per kilogram body weight.

An imaging study was performed in an adult albino rabbit weighing 4.2 kg after intravenous administration of 5 mCi of $^{99m}Tc$ IDP using the Searle Radiographics HP gamma camera fitted with a 140 kev high resolution parallel hole collimator. Images in the posterior projection were obtained from one to 24 hours after injection in three separate views collecting 300k counts for each. No attempts were made to remove the urine from the bladder during this study.

Because of the insignificant toxicological problems and high bone uptake of $^{99m}Tc$-IDP a volunteer patient was studied with this compound after informed consent was obtained. Fifteen mCi of $^{99m}Tc$-IDP containing 1.5 mg of tetrasodium imidodiphosphonate (equivalent to 1 mg of the acid) was intravenously injected in a 33-year-old female with a recent modified left radical mastectomy and whole body images of the patient in both anterior and posterior projections were obtained 3 hours after injection using and Ohio Nuclear Series 100 area scan scanning camera with a high sensitivity, low energy parallel hole collimator.

The results of the above tests are discussed below.

Table 1 contains biological distribution data of $^{99m}Tc$-IDP in rabbits with $^{85}Sr$ used simultaneously. The numbers shown in parenthesis after the time of study is the number of animals used per time interval. The values for each organ shown are the averages for each group of animals. The bone concentration shown as % dose / 1% body weight is the mean value of individual average of concentrations in four types of bone; the femur, tibia, spine and pelvis. An overall mean concentration of the four types of bone was calculated for each animal and then the average of these mean values were determined. Similarly the mean values for bone/organ ratios were calculated for each group.

Table 2 contains comparative data from this and other studies on the distribution of a variety of $^{99m}Tc$ labeled compounds in rabbits at 2 hours studied simultaneously with $^{85}Sr$. The numbers in parenthesis under each compound indicates the number of animals used for each group. The values known here have been derived from the data in the Subramanian et al references, supra, except for the IDP complex. Only the mean values of the $^{99m}Tc$-$^{85}Sr$ ratios for each organ are shown.

FIG. 1 consists of serial composite whole body images of the 4.2 kg weight adult rabbit injected with 5 mCi of $^{99m}Tc$-IDP at the various times indicated from 1 hour to 24 hours. Each whole body image is a composite of three separate images for each of which 300k counts were collected.

Figure 2:
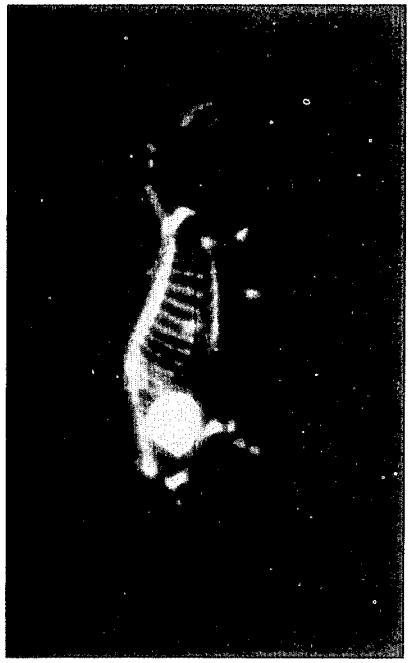

FIG. 2 shows the whole body image of the dog in the right lateral position at 4 hours after injection of 5 mCi of $^{99m}Tc$-IDP. The clear delineation of the vertebral column and all the ribs are quite apparent. The larger accumulation of the activity in the pelvic area is the urine in the bladder. At 4 hours as much as 50% of injected activity could be in the urine.

Figure 3:
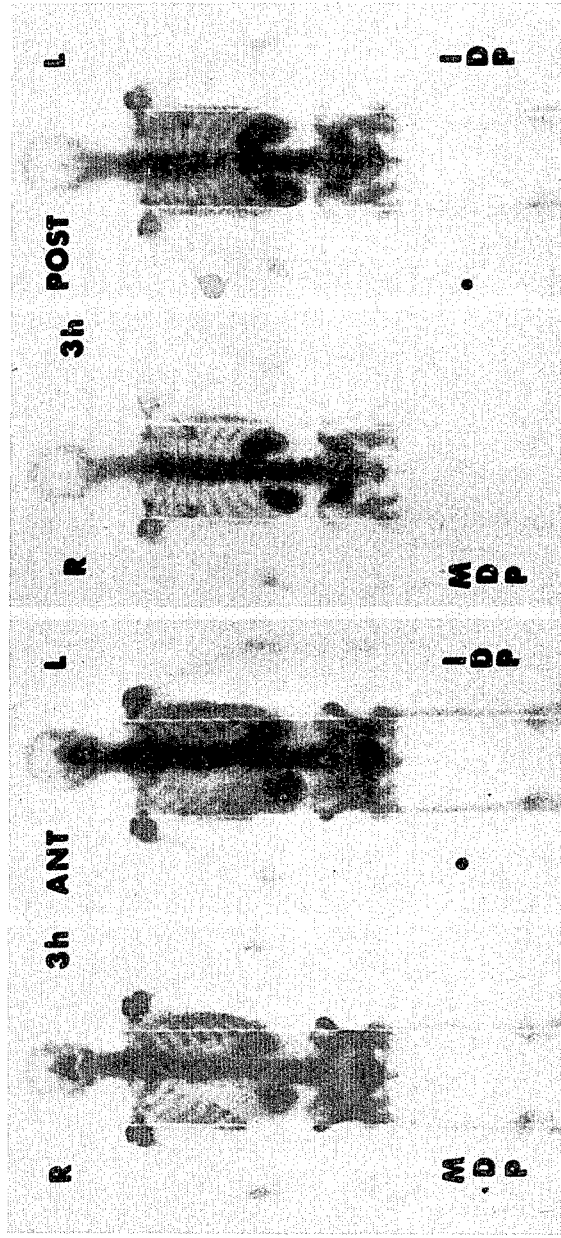

FIG. 3 illustrates comparative whole body images in the 33-year-old female patient obtained with both $^{99m}Tc$-MDP (methylene diphosphonate) and $^{99m}Tc$-IDP performed within a 10-day interval. These images were obtained with 15 mCi of each of the compounds and using an Ohio Nuclear whole body imaging camera as previously described. The count rates obtained with $^{99m}Tc$-IDP were approximately twice that of the MDP compound. Due to higher bone concentration and count rates the anterior image was obtained in 8.6 minutes with IDP versus 15.6 minutes with MDP using a data density of 200 for both. Similarly the posterior view took 8.2 minutes for IDP and 13.0 minutes for MDP.

In order to compensate for biologic variation, bone agents are best studied by comparing the quantitative uptake of the new compound with simultaneously administered $^{85}Sr$ as a means of normalization. In comparing several $^{99m}Tc$ labeled agents between each other one should not only compare the whole organ uptake of individual compounds but also the ratios of their concentrations with $^{85}Sr$, especially so in comparing bone uptakes. Table 1 illustrates the wide variation in concentrations in various types of bone. Due to regional variation in bone uptake with the skeleton it is difficult to correctly estimate whole body bone uptake quantitatively. Nevertheless, the data for single whole bones (femur and tibia) is useful. By comparing the bone uptake (Table 1) one can see that $^{99m}Tc$-IDP has approximately 25% more uptake than $^{85}Sr$ at earlier time intervals up to 2 hours and equivalent at later times. This concentration change over serial time intervals may be due to the metabolic breakdown of the compound at the bone mineral surface with the $^{99m}$Tc complex being more labile, while we known the biological half life of $^{85}$Sr is prolonged. Even at the later time intervals than 2 hours, $^{99m}$Tc-IDP concentration in bone is at least 20–25% higher than the other Tc complexes (Table 2). The soft tissue concentrations of all these complexes are lower, especially that of the muscle, than $^{85}$Sr. The liver concentration is somewhat higher than $^{85}$Sr for some $^{99m}$Tc complexes. This should not be a problem because the total liver concentration is relatively low. Overall, from the distribution studies in rabbits it may be inferred that the $^{99m}$Tc-IDP complex has the highest bone uptake of all the compounds reported.

The rabbit images shown in FIG. 1 clearly demonstrate the high skeletal localization of $^{99m}$Tc-IDP at 1 hour to 24 hours after injection of the compound. The details of all skeletal structure is very clearly delineated.

The dog image in FIG. 2 is also included to show the high quality of bone image that can be obtained with $^{99m}$Tc-IDP in a higher mammal than a rabbit.

After noting the increased bone uptake of $^{99m}$Tc-IDP in biodistribution studies and the safety of the compound (as demonstrated by toxicity studies) a volunteer patient was studied. FIG. 3 illustrates the whole body images both in the posterior and anterior projections of of this patient studied with $^{99m}$Tc-MDP and $^{99m}$Tc-IDP on separate days with the same dose and technique. The count rate with the IDP complex was approximately one and a half to two times that of the MDP compound. After the scans, individual images of selected areas were obtained with a stationary gamma camera. In these images, also done at similar time intervals, approximately 80 percent higher count rates were obtained with $^{99m}$Tc-IDP compared to the MDP complex. Much of this increased count rate may be accounted for by the 80% higher bone uptake noted with IDP than MDP in the tissue assay data. Part of this increased count rate could be attributed to the increased blood levels and soft tissue concentrations of the IDP complex (compared to MDP).

Since identical conditions were used for both the MPD and IDP complexes in this patient, a visual comparison of both the scans is possible. Clearly the $^{99m}$Tc-MDP images are superior.

Table 1

$^{99m}$Tc Labeled Stannous Imidodiphosphonate in Rabbits Simultaneous Study with $85_{Sr}$

| ORGAN | 15 min (6) | | 1 hour (6) | | 2 hours (9) | | 4 hours (9) | | 24 hours (7) | |
|---|---|---|---|---|---|---|---|---|---|---|
| | $99m_{Tc}$ | $85_{Sr}$ | $99m_{Tc}$ | $85_{Sr}$ | $99m_{Tc}$ | $85_{Sr}$ | $99m_{Tc}$ | $85_{Sr}$ | $99m_{Tc}$ | $85_{Sr}$ |
| % Dose in Whole Organ | | | | | | | | | | |
| BLOOD | 15.4 | 16.1 | 5.90 | 8.17 | 2.92 | 5.19 | 1.69 | 2.72 | 0.734 | 0.250 |
| LIVER | 4.24 | 2.13 | 2.08 | 1.58 | 2.00 | 0.947 | 1.58 | 0.576 | 0.661 | 0.004 |
| MUSCLE | 9.32 | 15.6 | 4.47 | 9.55 | 3.01 | 7.96 | 1.53 | 4.80 | 0.599 | 0.628 |
| KIDNEY | 5.52 | 1.27 | 4.75 | 0.938 | 4.39 | 0.638 | 2.90 | 0.267 | 2.19 | 0.022 |
| MARROW | 1.07 | 0.903 | 0.646 | 0.817 | 0.643 | 0.499 | 0.447 | 0.300 | 0.331 | 0.070 |
| URINE | 13.3 | 4.94 | 37.6 | 8.96 | 47.4 | 16.6 | 49.5 | 26.2 | — | — |
| WHOLE FEMUR | 0.782 | 0.741 | 1.46 | 1.27 | 2.06 | 1.67 | 1.81 | 1.84 | 1.67 | 1.55 |
| WHOLE TIBIA | 0.561 | 0.540 | 1.12 | 1.03 | 1.63 | 1.34 | 1.57 | 1.57 | 1.09 | 1.38 |
| % Dose/1% Body Weight* | | | | | | | | | | |
| BLOOD | 2.20 | 2.29 | 0.843 | 1.17 | 10.420 | 0.742 | 0.242 | 0.388 | 0.105 | 0.331 |
| LIVER | 1.40 | 0.692 | 0.674 | 0.489 | 0.734 | 0.357 | 0.491 | 0.168 | 0.225 | 0.016 |
| MUSCLE | 0.217 | 0.363 | 0.104 | 0.222 | 0.070 | 0.186 | 0.035 | 0.125 | 0.014 | 0.015 |
| KIDNEY | 11.8 | 2.68 | 8.14 | 1.54 | 8.02 | 1.1 | 5.41 | 0.488 | 4.63 | 0.067 |
| MARROW | 0.489 | 0.410 | 0.294 | 0.382 | 0.291 | 0.227 | 0.203 | 0.137 | 0.150 | 0.032 |
| LG INT | 1.03 | 1.79 | 0.491 | 0.961 | 0.331 | 0.762 | 0.142 | 0.421 | 0.049 | 0.088 |
| SM INT | 0.732 | 1.23 | 0.406 | 0.654 | 0.323 | 0.669 | 0.245 | 0.300 | 0.069 | 0.042 |
| FEMUR | 3.60 | 3.41 | 5.70 | 5.23 | 8.40 | 6.84 | 7.71 | 7.87 | 6.75 | 6.39 |
| TIBIA | 3.14 | 3.02 | 5.26 | 4.67 | 7.94 | 6.60 | 7.59 | 7.64 | 6.64 | 6.58 |
| PELVIS | 6.03 | 5.06 | 7.15 | 5.47 | 9.66 | 7.35 | 11.0 | 9.83 | 8.97 | 8.13 |
| SPINE | 3.63 | 3.76 | 6.23 | 5.82 | 9.25 | 8.05 | 8.97 | 9.57 | 6.96 | 6.96 |
| AVG BONE | 4.10 | 3.82 | 6.08 | 5.30 | 8.81 | 7.21 | 8.83 | 9.16 | 7.32 | 6.93 |
| RATIOS | | | | | | | | | | |
| BONE/BLOOD | 1.86 | 1.71 | 7.75 | 4.53 | 24.8 | 10.5 | 39.8 | 23.6 | 69.4 | 20.9 |
| BONE/MUSCLE | 18.7 | 10.6 | 68 | 23.9 | 177 | 44 | 288 | 73.3 | 528 | 462 |
| BONE/MARROW | 8.92 | 9.84 | 23 | 13.9 | 37 | 36 | 50 | 66.9 | 59 | 217 |

*% Dose/1% Body weight
$$= \frac{\frac{\% \text{ Dose in organ or sample}}{\text{Wt of organ or sample}}}{\text{Body weight}} \times 100$$

Table 2

COMPARATIVE RESULTS OF $99m_{Tc}$ LABELED BONE IMAGING AGENTS IN RABBITS. SIMULTANEOUS STUDY WITH $85_{Sr}$ AT 2 HOURS $99m_{Tc}/85_{Sr}$ RATIOS CALCULATED FROM SPECIFIC CONCENTRATIONS*

| Organ | IDP (9) | MDP (12) | EHDP (12) | Pyro Phosphate (12) | Poly Phosphate (12) | AEDP (6) | HMDTMP (6) | EDTMP (6) | DTPMP (6) |
|---|---|---|---|---|---|---|---|---|---|
| Blood | 0.552 | 0.371 | 0.362 | 0.703 | 1.48 | 0.416 | 0.703 | 0.881 | 0.461 |
| Liver | 2.12 | 0.568 | 0.954 | 0.779 | 2.61 | 0.766 | 0.855 | 1.78 | 0.544 |
| Muscle | 0.350 | 0.192 | 0.172 | 0.365 | 0.623 | 0.135 | 0.407 | 0.438 | 0.221 |

Table 2-continued

COMPARATIVE RESULTS OF $99m_{Tc}$ LABELED BONE IMAGING AGENTS IN RABBITS. SIMULTANEOUS STUDY WITH $85_{Sr}$ AT 2 HOURS
$99m_{Tc}/85_{Sr}$ RATIOS CALCULATED FROM SPECIFIC CONCENTRATIONS*

| Organ | IDP (9) | MDP (12) | EHDP (12) | Pyro Phosphate (12) | Poly Phosphate (12) | AEDP (6) | HMDTMP (6) | EDTMP (6) | DTPMP (6) |
|---|---|---|---|---|---|---|---|---|---|
| Kidney | 7.27 | 3.93 | 3.53 | 2.81 | 9.46 | 3.71 | 7.06 | 8.44 | 3.82 |
| Marrow | 1.24 | 0.617 | 0.814 | 0.726 | 2.95 | 0.852 | 0.713 | 1.22 | 0.547 |
| Femur | 1.23 | 0.820 | 0.796 | 0.710 | 0.826 | 0.641 | 0.434 | 0.677 | 0.419 |
| Tibia | 1.20 | 0.730 | 0.798 | 0.694 | 0.66 | 0.641 | 0.437 | 0.684 | 0.384 |
| Pelvis | 1.34 | 0.920 | 0.913 | 0.918 | 1.01 | 0.693 | 0.516 | 0.720 | 0.627 |
| Spine | 1.17 | 0.826 | 0.801 | 0.827 | 0.82 | 0.618 | 0.428 | 0.572 | 0.415 |
| Average Bone | 1.24 | 0.833 | 0.832 | 0.812 | 0.87 | 0.648 | 0.456 | 0.662 | 0.467 |

IDP = Imidodiphosphonate  
MDP = Methylene Diphosphonate  
EHDP = Ethylene Hydroxy Diphosphonate  
AEDP = Amino Ethylne Diphosphonate  
HMDTMP = Hexamethylene Diamino Tetra (Methylene Phosphonate)  
EDTMP = Ethylene Diamino Tetra (Methylene Phosphonate)  
DTPMP = Diethylene Triamino Penta (Methylene Phosphonate)  
Numbers in parenthesis under each compound indicates number of animals studied for that compound.

What is claimed is:

1. A bone-seeking composition suitable for use as a skeletal imaging agent comprising a technetium-99m-tin-imidodiphosphonate complex.

2. Stannous imidodiphosphonate complex.

3. A bone-seeking composition comprising a solution adapted for intravenous administration containing the composition of claim 1.

4. The composition of claim 3 in unit dosage form containing 5–20 mCi of radioactivity.

5. A method of preparing the composition of claim 1 comprising reducing a technetium-99m containing pertechnetate salt with stannous ion in an aqueous medium in the presence of imidodiphosphonic acid or a salt thereof.

6. The method of claim 5 comprising admixing in aqueous solution imidodiphosphonic acid or a salt thereof, a stannous salt and a technetium-99m containing pertechnetate salt.

7. The method of claim 5 comprising admixing technetium-99m containing pertechnetate salt with a stannous imidodiphosphonate complex in an aqueous medium.

8. The method of claim 5 wherein said pertechnetate salt is an alkali metal salt.

9. A method of skeletal-imaging which includes the intravenous administration of a solution adapted for intravenous administration containing the composition of claim 1.

10. The method of claim 9 wherein said solution is in unit dosage form of from 1 to 5 ml and contains 5–20 mCi of radioactivity.

11. The method of claim 10 wherein from about 0.05 to about 0.5 mg of complex are administered per kg of body weight, based on the weight of the free imidodiphosphonic acid.

* * * * *